(12) United States Patent
Sorensen et al.

(10) Patent No.: US 7,937,973 B2
(45) Date of Patent: May 10, 2011

(54) TUBULAR SPACER FABRIC

(75) Inventors: Bettina B. Sorensen, Silkeborg (DK); Samantha J. Garvey, Waterford (IE)

(73) Assignee: Tytex A/S, Ikast (DK)

( * ) Notice: Subject to any disclaimer, the term of this patent is extended or adjusted under 35 U.S.C. 154(b) by 88 days.

(21) Appl. No.: 11/659,183

(22) PCT Filed: Aug. 10, 2005

(86) PCT No.: PCT/DK2005/000523
§ 371 (c)(1),
(2), (4) Date: Sep. 8, 2008

(87) PCT Pub. No.: WO2006/015599
PCT Pub. Date: Feb. 16, 2006

(65) Prior Publication Data
US 2009/0126413 A1 May 21, 2009

(30) Foreign Application Priority Data
Aug. 12, 2004 (DK) .................. 2004 01219

(51) Int. Cl.
*D04B 1/22* (2006.01)
(52) U.S. Cl. ........................................ 66/196
(58) Field of Classification Search .............. 66/202, 66/195, 196, 193, 8
See application file for complete search history.

(56) References Cited

U.S. PATENT DOCUMENTS

| 2,067,739 | A | | 1/1937 | Tanski |
| 4,771,518 | A | | 9/1988 | La Pointe et al. |
| 5,334,442 | A | * | 8/1994 | Okamoto et al. ............. 442/224 |
| 5,651,847 | A | * | 7/1997 | Loeffler .............................. 66/19 |
| 5,735,145 | A | * | 4/1998 | Pernick ............................ 66/196 |
| 5,807,295 | A | | 9/1998 | Hutcheon et al. |
| 6,151,928 | A | * | 11/2000 | Anyon et al. ................... 66/196 |
| 6,779,369 | B2 | * | 8/2004 | Shepherd ........................ 66/196 |
| 6,854,296 | B1 | * | 2/2005 | Miller, III ....................... 66/190 |
| 2009/0126413 | A1 | * | 5/2009 | Sorensen et al. ............... 66/196 |

FOREIGN PATENT DOCUMENTS

| EP | 0 921 221 | 6/1999 |
| GB | 840523 | 11/1957 |
| GB | 960864 | 6/1964 |
| WO | WO-95/26698 | 10/1995 |
| WO | WO-00/13621 | 3/2000 |

* cited by examiner

*Primary Examiner* — Danny Worrell
(74) *Attorney, Agent, or Firm* — Edwards Angell Palmer & Dodge LLP; Peter F. Corless; Lisa Swiszez

(57) ABSTRACT

The present invention relates to a weft-knitted tubular spacer fabric for use in orthopaedic products comprising a first outer layer, a second outer layer, and an intermediate spacer layer integrated with said first and second outer layers, said tube having a length. According to invention the spacer fabric is knitted in a tubular form with a circumference less than 1000 mm, said tubular spacer fabric not being cut open in its length direction, thereby conforming seamlessly to a body part or limb of a wearer. Hereby, a tubular spacer fabric is obtained which most expediently conforms seamlessly to a body part or limb of a wearer. This has the advantage that the seamless tubular spacer fabric may be used directly as a wrap, a bandage, a support or may be used as liner under casting.

25 Claims, 2 Drawing Sheets

TUBULAR SPACER FABRIC

FIELD OF THE INVENTION

The present invention relates to a weft-knitted tubular spacer fabric for use in orthopaedic products comprising a first outer layer, a second outer layer, and an intermediate spacer layer integrated with said first and second outer layers, said tube having a length.

The weft-knitted spacer fabric according to the pre-sent invention may for instance be used in bone fracture stabilization and joint sprain management products for orthopaedic purposes, such as orthopaedic splinting, orthopaedic casting, orthopaedic bracing, prosthetic limbs or devices, orthopaedic soft goods and support as well as sports bracing and sports goods equipment and work wear, for preventive as well as for treatment purposes. Said product groups will in the following be referred to as orthopaedic applications or orthopaedic products.

BACKGROUND ART

Fabric-laminated foam materials, such as neoprene or polyurethane, are often used for a wide range of applications, such as wraps, supports, braces and other orthopaedic products.

For these applications it is of high importance that the materials have certain built-in properties. These properties may for instance be a cushioning effect for comfort, compression for support, as well as stabilizing a limb, a joint or another area of the human and/or animal anatomy.

Other examples are resiliency, elasticity or flexibility in order to provide orthopaedic products which may fit the wearer during movement or fit a large variety of wearers and at the same time provide the right amount of power, i.e. support and compression.

However, these fabric-laminated foam materials such as neoprene, have the disadvantages and drawbacks that they per se are substantially impermeable to air or gasses and moisture, and thereby not breathable, wherefore their use in orthopaedic products are not always favourable especially when used to cover for instance wounds or when used in athletic wraps or shoes. In order to improve the properties of the neoprene with regards to permeability perforations or holes are often provided in the material, however, scientific test have shown that knitted spacer fabrics are superior to perforated neoprene in relation to breathability and moisture permeability.

Therefore, textiles such as knitted stretchable spacer fabrics are more and more used instead of the above mentioned materials.

Furthermore, the anatomy of the wearer consist of many surfaces which have a double curvature form. Thus, in the prior art it is necessary to specially adapt for instance the orthopaedic product to these surfaces of double curvature for providing the right support and comfort for the wearer. This is in the prior art carried out by selecting several pieces of fabric having different properties or pieces of the same fabric cut at same or different shapes/angles/directions and subsequently adapting as well as form-fitting the pieces into an orthopaedic product.

Most of the products are produced from flat materials like fabric, foam or neoprene, and are then cut and sewn into anatomically conforming tubes. The thereby provided tube will then have at least one seam, welding or other assembly along the length direction of the limb, which may provide discomfort to the wearer.

There is thus a need for developing and providing a tubular spacer fabric, in which several different properties may still be incorporated, and which can be seamlessly fitted to or slipped on a person's limb.

Other relevant built-in properties may for instance be support, skin friendliness, breathability, moisture handling properties, protection from impact, rigidity and stiffness for supporting, stabilizing or immobilizing a limb, joint, muscle, bone or other body part.

For orthopaedic applications within support, splinting, bracing and casting, the textile or other soft materials used are often combined with additional stiffening elements in the form of rigid or semi-rigid supports, such as stays, polymer materials, impregnation resins, metal splints, plaster of pairs, fibreglass or the like. These elements can for example be coated or laminated on, sewn on, moulded on, welded on, riveted on or in other ways adhered to/assembled with the soft materials, or they can be separate and just used in conjunction with the softer materials.

In any case, the soft materials contribute with cushioning, softness, moisture handling, skin friendliness, breathability, support and the like, and the stiffening elements contribute with stiffness and further support.

During use of the brace or cast the combination of a rigid material with a conventional soft, e.g. foam padding, often traps or promotes heat and moisture in the skin area, which may lead to skin maceration and skin breakdown or possible skin infection.

Rigid braces and casts are often heavy and/or thick, due to the combination of large rigid parts with a thick cushioning inner layer and assembly means, and can thus be uncomfortable to the wearer. Some braces and most casts cannot be washed or in other ways exposed to humidity or water, due to the often moisture absorbing thick inner layers that will take a long time to dry and also due to the covering rigid brace that further slows down the water penetration, evaporation and drying speed. For example, showering or rainy weather can be a problem to the wearer, where the brace will have to be removed during showering, or the cast be temporary protected by a water-proof material, i.e. a sealed polybag, or direct contact with water simply have to be avoided.

A limited number of products exist that will actually allow the wearer to i.e. swim or shower with a cast, such as for instance the PTFE cast liner padding used in connection with fibreglass tape.

Furthermore, it is often important that the orthopaedic product is permeable to air and moisture. Often this is attempted to be obtained by providing perforations or holes in the stiffening and/or soft elements. This may be a further production step that makes the end products more expensive, unattractive, and often it does not ensure adequate breathability. An example of this is perforation of neoprene, where tests have shown that in spite of the perforation the breathability and moisture handling properties are often unsuitable for use for medical bandages or sports bandages, due to moisture build-up on the human skin, cf. the article "Physiological Demands on Materials for Bandages" of Dr. Volkmar T. Bartels and Prof. Dr. Karl-Heinz Umbach.

Orthopaedic support products exist in numerous variants for the different body parts, such as knee, foot, wrist, back, neck, elbow etc. In general they may consist of soft materials only or a combination of soft materials and stiffening elements, depending on the level of support and immobilizing needed. They may be adjustable (e.g. hook & loop closure) and may in some areas contain stiffening elements, such as semi-rigid or rigid stays, flexible hinges, polymer laminated materials or the like. The stiffening elements may be preshaped or be shapeable. The shapeable stiffening elements may expediently be moulded or formed for instance by hand to the body part to be supported, whereby a tight fit is obtained.

However, as mentioned above during the production of these orthopaedic products, the soft material, such as neoprene, laminated foam, elastic, felt or spacer fabric, is first cut out in one or more pieces having suitable size and form. The anatomically adapted shape of the support product is thereafter obtained by joining together, for instance by sewing, welding, gluing and/or moulding, the use of "Hook & loop" closures, and/or impregnating the different soft parts. During the joining or after, the stiffening elements are incorporated in the product by sewing, encapsulating, coating, laminating, welding or other methods. This involves many time-consuming processes and thereby makes the end product expensive. Furthermore the seams or joints can be uncomfortable and create pressure marks on the wearer's skin.

As mentioned above in the prior art the use of spacer fabrics in flat fabric form for orthopaedic products is known. Thus, in the prior art for a spacer fabric product to encapsulate or encircle a certain limb or body part, the spacer fabric has to have a seam or other joint along the length direction of the body part.

In order to limit the number of seams, joints and/or number of manufacturing steps, a need has risen for providing a seamless limbsize tubular spacer fabric wherein built-in properties, form and fit, are provided in as few manufacturing steps as possible.

SUMMARY OF THE INVENTION

An object of the present invention is to wholly or partly overcome the above disadvantages and drawbacks of the prior art. More specifically, it is an object to provide a spacer fabric, which is weft-knitted in a tubular form consisting of various circumferences to encirculate/accommodate the body, a body part or limb of the wearer.

It is furthermore an object of the present invention to provide a tubular weft-knitted spacer fabric having a circumference that allows it to conform to limbs or other body parts, encircling them seamlessly, preferably with a circumference less than 1000 mm.

Also it is an object of the present invention to provide a tubular spacer fabric having improved mechanical properties, such as elasticity, cushioning and recovery as well as having substantial isotropic properties.

A further object of the present invention is to provide a tubular spacer fabric which may directly be used and incorporated in orthopaedic products, such as wraps, supports, braces, casts or prosthetic limbs or devices. An additional object of the present invention is to provide a tubular spacer fabric which is cost-effective to produce in small amounts.

It is moreover an object of the present invention to provide a flexible tubular spacer fabric, wherein several and different mechanical, permeable and thermal properties may be incorporated in the same spacer fabric.

Still another object of the present invention is to provide a light-weight tubular spacer fabric.

It is also an object of the present invention to provide a tubular spacer fabric, wherein a large variety of yarns and monofilaments may be used.

A further object of the present invention is to provide a tubular spacer fabric, wherein at least a part of one of the outer layers may be stiffened.

Additionally, an object is to provide a tubular spacer fabric, which may easily be used and incorporated in orthopaedic products, with the involvement of only a few individual parts, and may be without additional rigid parts.

It is furthermore an object of the present invention to provide a tubular spacer fabric having permeable properties, such as breathability and good moisture handling properties, e.g. moisture permeability, moisture transportation, moisture resistance, quick drying and good washability.

The above objects, together with numerous other objects, advantages and features, which will become evident from the below description, are accomplished by a solution in accordance with the present invention by the weft-knitted spacer fabric is knitted in a tubular form with a circumference less than 1000 mm, said tubular spacer fabric not being cut open in its length direction, thereby conforming seamlessly to a body part or limb of a wearer.

Hereby, a tubular spacer fabric is obtained which most expediently conforms seamlessly to a body part or limb of a wearer. This has the advantage that the seamless tubular spacer fabric may be used directly as a wrap, a bandage, a support or may be used as liner under casting.

Furthermore, the seamless tubular spacer fabric may also be breathable, be water and moisture resistant so that it would be possible to use the tubular spacer fabric as a cast padding in wet or humid environments or during sports activities, where heavy sweating may occur.

The term "tubular" is in this context to be construed as the spacer fabric having a form as a tube with an optional geometric configuration seen in the cross sectional direction of the fabric. The geometric configuration may for instance be circular, elliptic, square, buttonhole shaped or other relevant geometric configurations.

The first outer layer may advantageously be the outer surface of the seamless tubular spacer fabric and the second outer layer may be the inner surface of the seamless tubular spacer fabric or vice versa.

The term "circumference" is in this context to be construed as being the extension or distance measured around or along the periphery of the seamless tubular spacer fabric seen in a cross sectional view. For instance the circumference of a circle is πd, where π is phi and d is the diameter of the circle. However, a more practical manner to measure the circumference of the seamless tubular spacer fabric is to place the seamless tubular spacer fabric on a flat surface and subsequently flatten the tube (while it is still in a relaxed state, i.e. without any tension), so that it becomes two-folded and essentially flat. Hereby is it possible to measure the width of the fabric and afterwards to multiply the width with the factor two, thus obtaining substantially the circumference of the seamless tubular spacer fabric in question.

The circumference of the seamless tubular spacer fabric and the elastic properties may vary along the length direction of the seamless tubular spacer fabric.

The term "is knitted" is in this context to be construed as the spacer fabric being substantially knitted in a tubularly form in one piece without subsequently processing steps, such as joining, cutting or sewing in the length direction.

The term "seamless" is in this context to be construed as the tubular spacer fabric is provided without any seams or joints in the length direction of the spacer fabric. However, it should be understood that the tubular spacer according to the invention may have seams or joints in the transverse direction of the spacer fabric, for instance at the ends or at the edges. Furthermore, it should be understood that within the inventive idea one or more accessory(ies), such as for instance rigid stays, may be applied to the spacer fabric by for instance sewing, also in the length direction.

According to the invention the circumference may be between 50 mm and 785 mm. Hereby a tubular spacer fabric is obtained, which may directly be used in a limb orthopaedic product substantially without any further processing steps, directly complying to the contours of the human body parts joint, limb, etc.

All numeral dimensions mentioned in present description are taken in a relaxed state of the fabric, i.e. without any tension exerted on the fabric.

Advantageously, the circumference may be different along the length of the seamless tubular spacer fabric. The different circumferences of the seamless tubular spacer fabric may relate to different sizes of the wearer or different limbs or body parts of the wearer, i.e. finger, wrist, lower arm, upper arm, elbow, lover leg, upper leg, knee, foot, toe, back, neck, upper head etc. A flexible seamless tubular spacer fabric is thereby obtained which may be adapted to provide the right amount of support in the specific areas of the anatomy.

For instance the seamless tubular spacer fabric may have a conical form. The stretch properties or dimensions of the fabric may also be varied in certain areas by increasing or decreasing the stitch length or knitting tension.

Furthermore, the intermediate layer may be adapted to transport moisture to the outer layers, so that moisture is transported away from the skin of the wearer, whereby the risk of skin maceration is avoided or at least substantially reduced.

According to the invention the first and/or second outer layer may comprise yarns comprising polyurethane, such as Elastane, up to 40% of total fabric weight. Hereby an elastic seamless tubular spacer fabric is achieved, wherein several and different properties may be built-in such as cushioning, elasticity, support and/or recovery and wherein substantially isotropic properties. The term "isotropic" is in this context to be construed as the seamless tubular spacer fabric having substantially the same physical properties when measured in different directions of the fabric.

Accordingly, the elastic seamless tubular spacer fabric may in an expedient manner be incorporated in orthopaedic products, such as supports wherein a so-called "4-way" stretch flexibility is necessary. The elastic seamless tubular spacer fabric thereby secures that the orthopaedic product always provides good support and comfort to the wearer also during movement. Furthermore, no additional form-fitting of the orthopaedic product to the surface of double curvature of the body of the wearer is required and thereby further processing steps (as known in prior art) are avoided.

Advantageously, the Elastane may be up to 40% of total fabric weight. Thereby the seamless tubular spacer fabric is provided with a high elasticity as well as support suitable for different purposes. According to the invention the higher the content of Elastane is the tighter the fabric structure becomes and the steeper the intermediate yarn stands between the outer layers, whereby the cushioning increases. The content of Elastane in relation to the total fabric weight may even be higher than 40%.

Advantageously different Elastane contents may be used in different areas of the seamless tubular spacer fabric, whereby different stretch properties may be obtained in different areas of the seamless tubular spacer fabric. This may for instance be obtained by varying the knitting structure and yarn components.

The intermediate spacer layer may comprise monofilament and/or multifilament pile yarns.

Advantageously, according to the invention the yarns of the outer layers may comprise Elastane, polyester, polyamide, polypropylene, wool, cotton or viscose or a combination thereof.

The pile yarns of the intermediate spacer layer may expediently comprise polyester, polyamide, polypropylene, wool, cotton or viscose or a combination thereof.

Advantageously the intermediate spacer layer may according to the invention comprise yarns adapted to have a rapid drying when exerted to moisture. Thereby it is obtained that the seamless tubular spacer fabric may be used in wet environments, for instance during showering of the wearer. Such yarns may for instance be coarse filamented or made water repellent i.e. by hydrophobic finishing.

According to the invention the pile yarns of the intermediate spacer layer create channels or spaces filled with air so that light weight and breathability properties of the spacer fabric is obtained. Furthermore this provides the capability of fast drying to the fabric as well as capability of leading moisture away from the skin.

In an expedient embodiment according to the invention the seamless tubular spacer fabric may have a thickness from 1 mm to 7 mm, preferably from 3 mm to 5 mm. The thickness may be varying along the length and/or the circumference of the seamless tubular spacer fabric, i.e. by using different knitting structures, yarns or stitch lengths. Hereby is obtained a flexible seamless tubular spacer fabric which may be designed specifically to the requirement of use as well as have incorporated different properties such as flat areas, resiliency or added cushioning in different areas of the seamless tubular spacer fabric.

In an expedient manner the intermediate spacer layer may be excluded in a predetermined area of the seamless tubular spacer fabric, and the two outer layers may instead be interknitted directly to each other, with the intermediate yarns running flat between them. Especially in certain specific applications of the seamless tubular spacer fabric, for instance for a wrist brace, it may advantageously to exclude the monofilament pile yarns in certain areas. A predetermined area in an orthopaedic wrist or lower arm product could for instance be the area, where an opening for the thumb is provided. The ends of the monofilament pile yarns possess the disadvantage that they provide discomfort to the wearer when the edge of the fabric is exposed to the skin. So by excluding the intermediate spacer layer as mentioned above around the area of the thumb a better comfort of the wearer is obtained. A further advantage is that less manufacturing steps are necessary for producing the orthopaedic product.

According to the invention the inner surface of the tubular spacer fabric may comprise yarns made of skin-friendly material especially when being used as for instance a liner or a padding under a cast.

According to the invention at least one of the outer layers may comprise friction enhancing means, in order to provide fixation properties to the orthopaedic product, so that it will stay in place on the skin of the wearer, or for instance rigid parts on the outside also may stay in place.

In a preferred embodiment according to the invention the number of courses per cm in the outer layers may be from 5 to 40, preferably from 10 to 15, and the number of wales per cm in the outer layers is from 8 to 20, preferably from 10 to 15, whereby a spacer fabric having a high density is obtained.

In an embodiment according to the invention at least one of the outer layers may comprise a knitting structure with holes, jacquards or other patterns.

Advantageously the outer surface of the tubular spacer fabric may comprise yarns made of a material, which is adapted to stiffening, for instance when treated with resin. In addition it is possible to use the tubular spacer fabric as an actual cast or other rigid part by subsequently treating it with resin enabling at least part of the fabric to become completely rigid, therefore being the "actual cast" or rigid part rather than just the padding or liner.

Furthermore, the tubular form of the spacer fabric may be used to manufacture an orthopaedic product or liner without seams and/or joints in the length direction.

In an expedient embodiment according to the invention at least one of the outer layers may comprise at least partly means for stiffening and/or hardening the outer layer.

BRIEF DESCRIPTION OF THE DRAWINGS

The invention and its many advantages will be described in more detail below with reference to the accompanying schematic drawings, which for the purpose of illustration show some non-limiting embodiments and in which.

All the figures are highly schematic and not necessarily to scale, and they show only parts, which are necessary in order to elucidate the invention, other parts being omitted or merely suggested.

DESCRIPTION OF PREFERRED EMBODIMENTS

Figure 1:
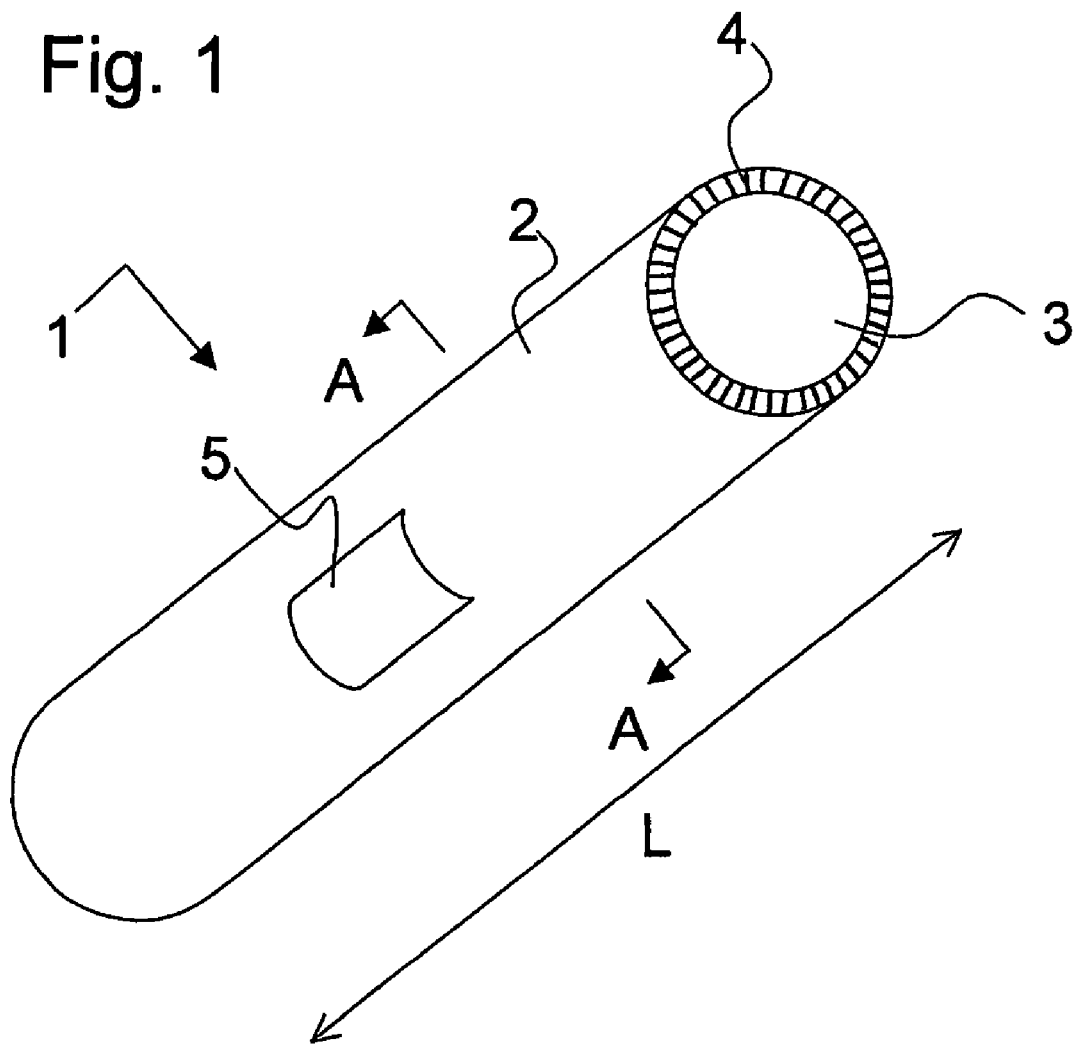
FIG. 1 shows a schematically perspective view of a seamless tubular spacer fabric according to the invention.

The seamless tubular spacer fabric 1 is shown schematically in FIG. 1. The weft-knitted seamless tubular spacer fabric 1 for use in orthopaedic products comprises a first outer layer 2, a second outer layer 3, and an intermediate spacer layer 4 integrated with said first 2 and second outer 3 layers.

According to the shown embodiment the first outer layer 2 is the outer surface of the seamless tubular spacer fabric 1 and the second outer layer 3 is the inner surface of the seamless tubular spacer fabric.

According to the invention the circumference of the seamless tubular spacer fabric 1 is less than 1000 mm, preferably between 50 mm and 785 mm.

The seamless tubular spacer fabric 1 is in this embodiment shown with a length L. During manufacturing of the seamless tubular spacer fabric the length L may be predetermined dependent on the specific application. During other applications the manufactured seamless tubular spacer fabric may be wound endlessly around for instance a drum or roll thereby enabling the user to optionally decide on the length in accordance with the specific application. This is especially useful if the seamless tubular spacer fabric is to be used as a liner or a padding under casting.

Figure 2:
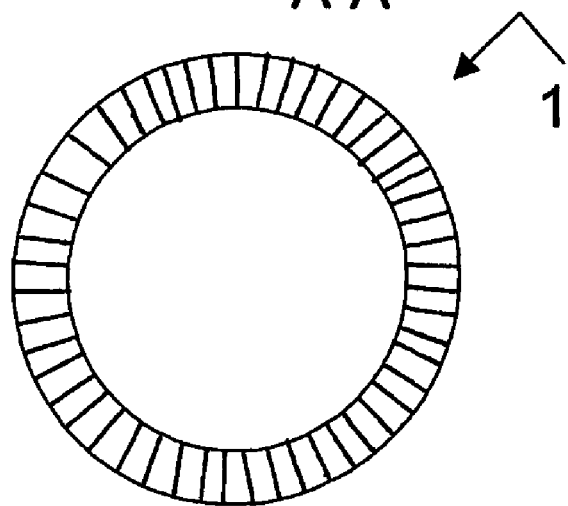
FIG. 2 shows a cross-sectional view taken by line AA of the seamless tubular spacer fabric.

FIG. 2 shows in cross-section one embodiment of the geometric configuration of the seamless tubular spacer fabric 1. In this embodiment the configuration is circular, however within the inventive idea the geometric configuration may as well be elliptic, buttonhole shaped or other relevant geometrical configurations and the circumference may vary along the length direction of the tubular spacer fabric.

A part 5 of the seamless tubular spacer fabric 1 is shown broken away in FIG. 3 and will be explained in more detail below.

According to the invention the outer layers 2; 3 of the seamless tubular spacer fabric 1 are knitted of yarns having a yarn count of 60 dTex to 200 dTex, and said outer layers 2; 3 may also in some instances comprise polyurethane, such as Elastane, up to 40% of total fabric weight.

The integration of the Elastane in the outer layers 2, 3 provides "power" to the seamless tubular spacer fabric 1. By power is meant elasticity and resiliency. Advantageously, the yarns of the outer layers 2;3 may comprise Elastane, polyester, polyamide, polypropylene, wool, cotton or viscose or a combination thereof so as provide surfaces to the seamless tubular spacer fabric 1, which are resistant to hook/loop attachments, or which have permeability, moisture/vapour transmission or wicking ability. By using yarns of micro fibre, cotton or viscose in one of the outer layers 2; 3—for instance the inner surface—a more soft, skin friendly and high comfort surface of the tubular spacer fabric 1 may be obtained.

The intermediate spacer layer 4 may according to one embodiment comprise monofilament and/or multifilament pile yarns having a yarn count of 22 dTex to 200 dTex. The intermediate spacer layer 4 is adapted to provide a cushioning effect to the seamless tubular spacer fabric 1. The pile yarns of the spacer layer 4 are interknitted in the spacer fabric 1 so as to provide a fixation of the two outer layers 2;3 in relation to each other.

Furthermore, the intermediate spacer layer 4 confers high compression resistance to the seamless tubular spacer fabric 1. Tests have shown that by using the weft-knitting method as well as pile yarns having a yarn count of 22 dTex to 200 dTex a compression stress for 40% compression of the seamless tubular spacer fabric 1 from 25 kPa to 150 kPa, preferably from 50 kPa to 100 kPa may be obtained.

Figure 4:
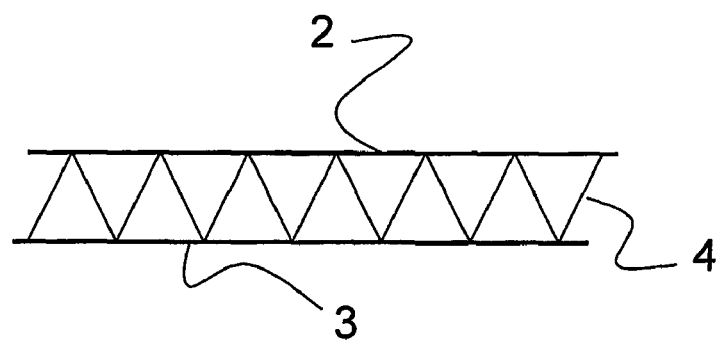
FIG. 4 shows a cross-sectional view taken by line B-B of the spacer fabric shown in FIG. 3.

According to an embodiment of the invention the number of pile yarns in the intermediate spacer layer 4 may be from 125 to 800 yarns per square cm. Furthermore, the pile yarns according to weft-knitting method may be individually spaced apart and preferably may be arranged so as to provide a steep V- or X-shape, when shown in a cross-sectional view, as for instance in FIG. 4. Preferably, a large part of the pile yarns is arranged in this V- or X-shaped formation so as to achieve a so-called lattice structure of the intermediate spacer layer 4 and thereby improving the resistance against collapsing when exerted with compressive forces, but still feel comfortable and cushioning.

Expediently, the pile yarns of the intermediate spacer layer 4 may comprise polyester, polyamide or polypropylene or a combination thereof.

Figure 3:
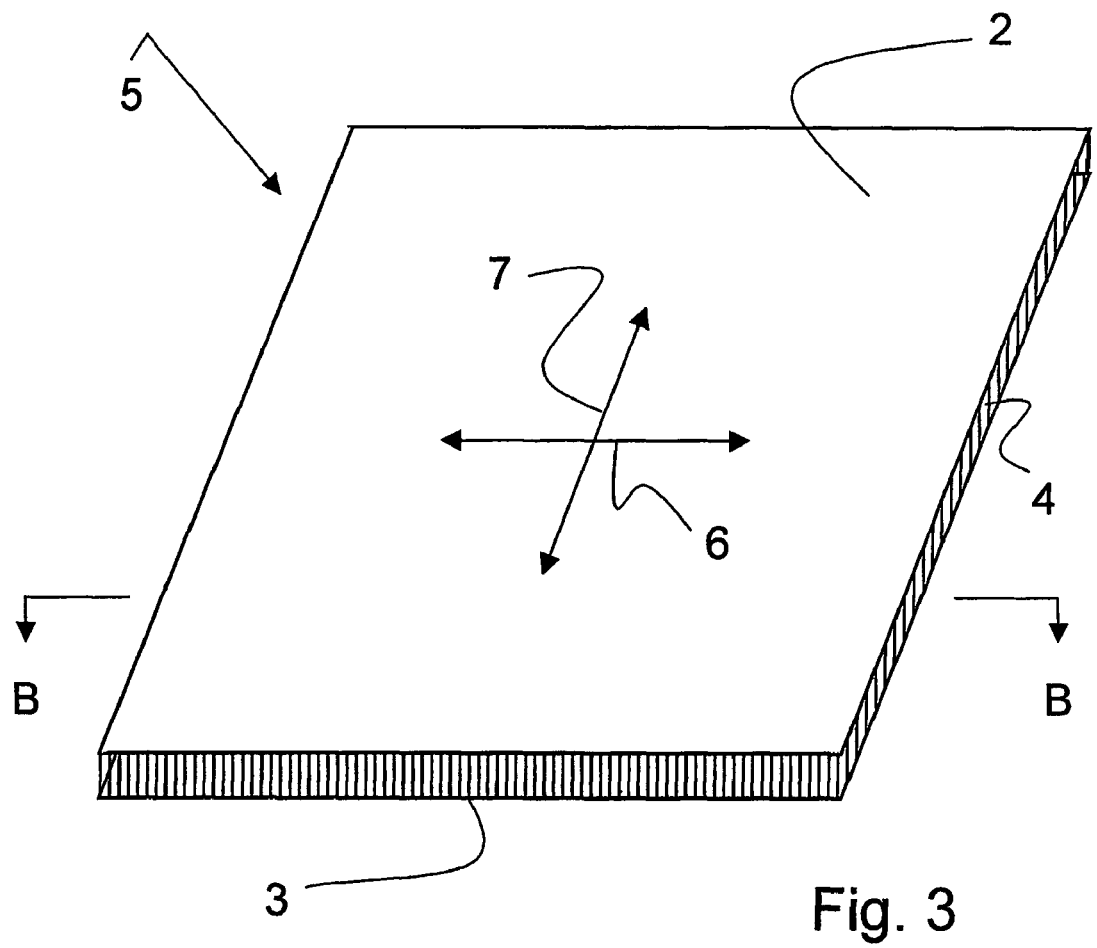
FIG. 3 shows a part of the seamless tubular spacer fabric according to the invention in perspective.

In FIG. 3 a double arrow 6 is furthermore shown, which illustrates the tension stresses in the transverse direction of the part 5 of the tubular spacer fabric. In the same way arrow 7 illustrates the tension stresses in the longitudinal direction. The difference in the tensile strength between a longitudinal direction (arrow 7) and a transverse direction (arrow 6) of the part 5 of the tubular spacer fabric may in one embodiment be less than 30%, preferably less than 20%.

As mentioned above FIG. 4 shows a schematic cross-sectional view taken along line B-B of the part 5 of the tubular spacer fabric shown in FIG. 3. By this cross-sectional view the lattice structure of the pile yarns of the intermediate spacer layer 4 is shown.

Furthermore, recovery of the mechanical properties of the seamless tubular spacer fabric 1 is important. Said recovery property may be thickness recovery for enabling the seamless tubular spacer fabric 1 to restore its cushioning effects, after a compressive force has been exerted on the surface. Among other recovery properties to be mentioned is elasticity recovery in a longitudinal and transverse direction of the seamless tubular spacer fabric 1 and compression recovery.

The thickness of the seamless tubular spacer fabric 1 may be from 1 mm to 7 mm, preferably from 3 mm to 5 mm. However, the thickness may also be as high as 10 mm to 12 mm for certain applications, though, the thickness from 3 mm to 5 mm is most useful as the seamless tubular spacer fabric is to be incorporated into and used for orthopaedic products.

According to the invention the seamless tubular spacer fabric may be used for orthopaedic products or other medical supports. Furthermore it may be used for wraps and support devices for human joints and limbs for athletic injury prevention and/or medical applications. The inventive seamless tubular spacer fabric may as well be used for orthopaedic purposes such as orthopaedic splinting, orthopaedic casting, orthopaedic bracing, prosthetic limbs or devices, orthopaedic soft goods and support, for preventive as well as for treatment purposes or for protective or preventive sports wear and/or sporting goods equipment and/or work wear.

Advantageously, it may be used for limb-conforming liner under casts or even a cast itself. Advantageously, the seamless tubular spacer fabric cushioning properties provide a cast padding, whereby the prior art padding under casts is avoided by using the inventive spacer fabric.

By the invention it is thereby achieved that several properties such as rigid, cushioning, soft, skin-friendly, moisture handling and light-weight, may be provided in substantially one manufacturing step in one seamless tubular spacer fabric, which thereby may be used directly without further preparation in orthopaedic products. Accordingly the product is less time-consuming to manufacture.

Additionally it is obtained that it is possible to make only a part of the outer layers or only one of the outer layers rigid and let others remain soft. It is further achieved by the invention that the stiffened outer layer has a good breathability.

Furthermore, the seamless tubular spacer fabric may be processed further after the knitting manufacturing step. It may for instance be coated, laminated, sprayed, immersed, dipped or the like for providing the seamless tubular spacer fabric with a coating or membrane. The coating or membrane may enhance certain properties, such as rigidity, moisture handling properties, comfort, etc.

In addition, the seamless tubular spacer fabric may also be further shaped after the knitting manufacturing step. It may for instance be shaped by means of thermo shaping, moulding, heat setting, shrinking, shaping on/in a mould, etc.

Although the invention above has been described in connection with preferred embodiments of the invention, it will be evident for a person skilled in the art that several modifications are conceivable without departing from the invention as defined by the following claims.

What is claimed is:

1. A weft-knitted spacer fabric for use in orthopaedic products, comprising a first outer layer, a second outer layer, and an intermediate spacer layer integrated with said first and second outer layers, wherein the first and second outer layers comprise yarns having a yarn count of 60 dtex to 200 dTex, the intermediate spacer layer comprises pile yarns having a yarn count of 22 dTex to 200 dTex, said spacer fabric having a length, wherein said spacer fabric is knitted in a seamless tubular form with a circumference less than 1000 mm, said tubular spacer fabric not being cut open in its length direction, thereby conforming seamlessly to a body part or limb of a wearer.

2. The weft-knitted spacer fabric as claimed in claim 1, wherein the circumference is preferably between 50 mm and 785 mm.

3. The weft-knitted spacer fabric as claimed in claim 1 or 2, wherein the circumference is different along the length of the tubular spacer fabric.

4. The weft-knitted spacer fabric as claimed in claim 3, wherein the tubular spacer fabric has a conical form.

5. The weft-knitted spacer fabric as claimed in claim 1, wherein the intermediate layer is adapted to transport moisture from the inner layer to the outer layer.

6. The weft-knitted spacer fabric as claimed in claim 1, wherein said first and/or second outer layer comprise yarns comprising polyurethane, such as Elastane, up to 40% of total fabric weight.

7. The weft-knitted spacer fabric as claimed in claim 1, wherein the intermediate spacer layer comprises monofilament and/or multifilament pile yarns.

8. The weft-knitted spacer fabric as claimed in claim 1, wherein the yarns of the outer layers comprise Elastane, polyester, polyamide, polypropylene, wool, cotton or viscose or a combination thereof.

9. The weft-knitted spacer fabric as claimed in claim 1, wherein the pile yarns of the intermediate spacer layer comprise polyester, polyamide or polypropylene or a combination thereof.

10. The weft-knitted spacer fabric as claimed in claim 1, wherein at least the first outer layer and the intermediate spacer layer comprise yarns adapted to have a fast drying rate when exerted to moisture.

11. The weft-knitted spacer fabric as claimed in claim 1, wherein the yarns of the intermediate spacer layer are interknitted with the yarns of the outer layers, so that distances are provided between the yarns in the intermediate spacer layer.

12. The weft-knitted spacer fabric as claimed in claim 1, wherein the tubular spacer fabric has a thickness from 1 mm to 7 mm, preferably from 3 mm to 5 mm.

13. The weft-knitted spacer fabric as claimed in claim 12, wherein the thickness is varying along the length and/or the circumference of the tubular spacer fabric.

14. The weft-knitted spacer fabric as claimed in claim 1, wherein the intermediate spacer layer is substantially flat in a predetermined area of the tubular spacer fabric.

15. The weft-knitted spacer fabric as claimed in claim 1, wherein the first outer layer is the outer surface of the tubular spacer fabric, and the second outer layer is the inner surface of the tubular spacer fabric.

16. The weft-knitted spacer fabric as claimed in claim 15, wherein the inner surface comprises yarns made of skin friendly material.

17. The weft-knitted spacer fabric as claimed in claim 15, wherein the outer surface comprises yarns made of material which is adapted to stiffening.

18. The weft-knitted spacer fabric as claimed in claim 1, wherein at least one of the outer layers comprises friction enhancing means.

19. The weft-knitted spacer fabric as claimed in claim 1, wherein the number of courses per cm in the outer layers may be from 5 to 40, and the number of wales per cm in the outer layers is from 8 to 20.

20. The weft-knitted spacer fabric as claimed in claim 1, wherein at least one of the outer layers comprises a knitting structure with holes, jacquards or other patterns.

21. The weft-knitted spacer fabric as claimed in claim 1, wherein the tubular form of the spacer fabric is being used to manufacture an orthopaedic product or liner without seams or joints in the length direction.

22. The weft-knitted spacer fabric as claimed in claim 1, wherein at least one of the outer layers at least partly comprises means for stiffening and/or hardening the outer layer.

23. The weft-knitted spacer fabric according to claim 19, wherein the number of courses per cm in the outer layers is from 10 to 15.

24. The weft-knitted spacer fabric according to claim 19, wherein the number of wales per cm in the outer layers is from 10 to 15.

25. The weft-knitted spacer fabric according to claim 1, wherein the pile yarns of the intermediate spacer layer are monofilament or multifilament pile yarns.

* * * * *